United States Patent [19]

Ward

[11] Patent Number: 4,747,777

[45] Date of Patent: May 31, 1988

[54] DENTAL INSTRUMENT

[76] Inventor: Ridley C. Ward, 2392 Fiesta Dr., Sarasota, Fla. 33581

[21] Appl. No.: 41,462

[22] Filed: Apr. 23, 1987

[51] Int. Cl.⁴ .............................................. A61C 3/00
[52] U.S. Cl. ..................................... 433/141; 433/39
[58] Field of Search ............... 433/141, 144, 148, 149, 433/39

[56] References Cited

U.S. PATENT DOCUMENTS

| | | | |
|---|---|---|---|
| 881,722 | 3/1908 | Sausser | 433/39 |
| 1,743,154 | 1/1930 | Meyer | 433/141 |
| 1,833,247 | 11/1931 | Fust | 433/39 |
| 4,270,902 | 6/1981 | Wiland | 433/144 |

Primary Examiner—John J. Wilson
Attorney, Agent, or Firm—Charles J. Prescott

[57] ABSTRACT

A dental instrument for assisting in the placement of a dental matrix band around a tooth to be repaired and the associated gingival margin of the repair. The dental matrix includes an elongated slender handle having a thin guide blade disposed from at least one end of the handle. The guide blade is adapted to be fitted between the matrix band and the tooth to be repaired to facilitate positioning of the matrix band over the gingival shoulder of the repair, then progressively around the tooth. The guide blade is preferably tapered toward its distal end, having a generally curved transverse section to mate against the side of the tooth. The guide blade may also include matrix band engaging means for providing positive connection between the matrix band and the matrix band during manipulation of the guide blade toward the patient's gums and the base of the tooth for enhanced positive and quick disposition of the matrix band.

8 Claims, 1 Drawing Sheet

U.S. Patent May 31, 1988 4,747,777
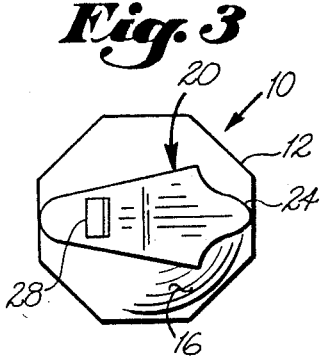
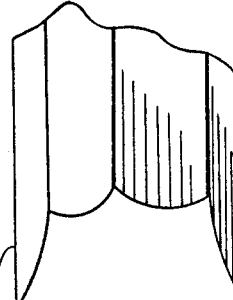
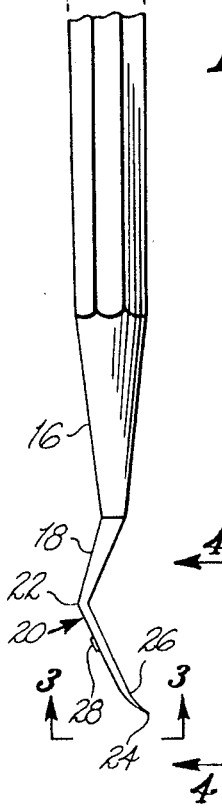
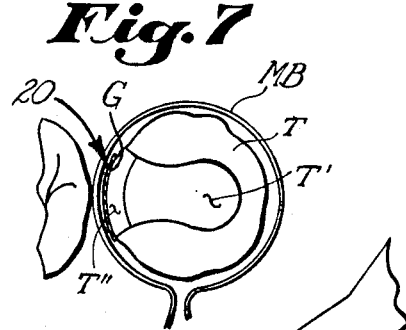
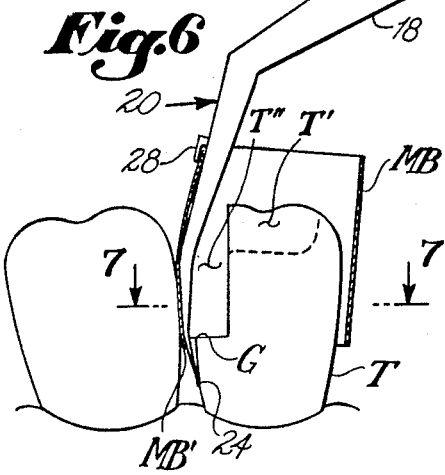
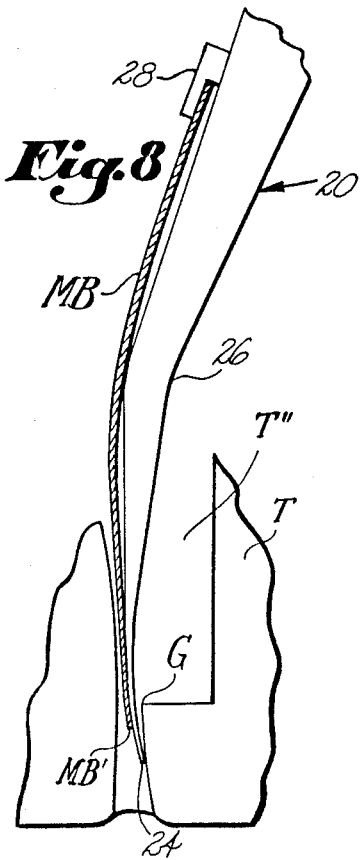

DENTAL INSTRUMENT

BACKGROUND OF THE INVENTION

This invention relates generally to the temporary installation of dental matrix bands, and more particularly to devices for facilitating the easy and quick installation of such bands prior to effecting repair of the teeth.

Matrix bands are used extensively by dentists in repairing teeth, which repair includes the initial step of grinding away sufficient portions of the decayed portions of a tooth to result in an opening through any of the vertical wall surfaces of the tooth. After such decayed or damaged tooth removal, a matrix band is typically applied to fit circumferentially around the entire tooth and down to the gumline of the tooth, whereupon the matrix band is tightened around the entire tooth and held thusly under hoop stress. This configuration and arrangement provides a dam-like mold adjacent the opening in the wall of the tooth against which a filling material such as an amalgam may be compacted.

Modern matrix bands are formed of a thin strip of foil-like surgical stainless steel into a band which may be split at one point to include a retaining appliance for providing the tightening hoop stress previously described.

Because of the thinness and overall dimensions of such matrix bands, many times during installation as the matrix band is progressively positioned over the gingival margin of the prepared repair site, the band will catch at that point and require further tedious multi-fingered manipulation of the band to successfully further move the matrix band to its final position at the base of the tooth against the gums before tightening.

No instrument known to applicant has been provided or is known to applicant, except for the present invention, which in any way obviates the cumbersome and tedious manipulation which is typically required to effect the progressive movement of the matrix band into its repair position once it has caught on the gingival margin of the tooth repair site.

The present invention provides a dental instrument which facilitates the easy installation of matrix bands over the shoulder formed at the gingival margin caused by the removal of deteriorated tooth material. This invention easily and conveniently guides the lower margin of the matrix band over this gingival margin shoulder and then continues to progessively carry the matrix band to its seated position at the base of the tooth to be repaired and against the gums. The invention may also be provided in an array of positionings and configurations for the guide blade in relation to the handle of the invention such that gingival margin shoulders formed by deteriorated tooth removal at any side of the tooth may be conveniently bridged by the invention being placed and manipulated between the matrix band and the repair site.

BRIEF SUMMARY OF THE INVENTION

This invention is directed to a dental instrument for assisting in the placement of dental matrix bands around teeth to be repaired and the associated gingival margin of the repair. The dental instrument includes a slender elongated handle having a thin guide blade disposed from at least one end of the handle. The guide blade is adapted to be fitted between the matrix band and the tooth to be repaired to facilitate positioning of the matrix band over the gingival shoulder of the repair, then progressively around the tooth. The guide blade is preferrably tapered toward its distal end, having a generally curved transverse section to mate against the side of the tooth. The guide blade may also include matrix band engaging means for providing positive connection between the convex side of the matrix band and the guide blade during maniuplation of the matrix band toward the patient's gums and the base of the tooth for enhanced positive and quick disposition of the matrix band.

It is therefore an object of this invention to provide a dental instrument which will facilitate the installation of a dental matrix by the elimination of interference of the dental matrix at the gingival shoulder of the repair site.

It is another object of this invention to provide a dental instrument which positively engages the dental matrix to assist in the progressive positioning of same around the base of a tooth to be repaired and against the gums of the patient.

It is another object to provide the above invention in variations adapted to repair sites on all sides of a tooth to be repaired.

In accordance with these and other objects which will become apparent hereinafter, the instant invention will now be described with reference to the accompanying drawings in which:

BRIEF DESCRIPTION OF THE DRAWINGS

FIG. 1 is a side elevation view of the handle and one end of the invention.

FIG. 2 is a front elevation view of the lower end of FIG. 1.

FIG. 3 is an enlarged view in the direction of arrows 3—3 in FIG. 1.

FIG. 4 is an enlarged view in the direction of arrows 4—4 in FIG. 1.

FIG. 5 is an enlarged perspective view of one end of the invention.

FIG. 6 is a side elevation partial section view of the invention in use.

FIG. 7 is a section veiw in the direction of arrows 7—7 in FIG. 6.

FIG. 8 is an enlarged view of FIG. 6 showing the invention in use in relation to a matrix band and the tooth to be repaired.

DETAILED DESCRIPTION OF THE INVENTION

Referring now to the drawings, and particularly to FIGS. 1-5, the invention is shown generally at numeral 10 and includes a slender, elongated handle 12 having tapered portions 14 and 16 disposed from the cylindrical mid-portion of the handle 12 as shown. Disposed from each tapered portion 14 and 16 is a matrix band guide blade shown generally at numeral 20. It should here be noted that the guide blade 20 may be disposed identically from tapered section 14 and 16 or, alternately and preferably, disposed at a somewhat different angle to provide a dental instrument adapted for use in conjunction with installation of a matrix band around a tooth in conjunction with repair on at least two different sides of a tooth.

Focusing more closely on the guide blade 20, it comprises a first offset 18, then a reverse transverse bend at 22 followed by another slight transverse bend 26 in the same direction at 26 as shown. The glide blade 20 is generally relatively rigid and of a very thin uniform cross section and having a narrower mid-portion in the vicinity of bend 22, broadening to bend 26, and then narrowing to tip 24 which is generally pointed, although slightly radiused.

Disposed from the back or convex side of the blade guide 20 is bracket or lip 28 which is provided to serve as means for engaging a matrix band during its installation as will be described herebelow. Although this bracket 28 is shown as an outwardly extension from the convex surface of blade guide 20, it may also be in the form of a groove or slight recess sufficient to perform a similar function as again herebelow described.

Referring now also to FIGS. 6, 7 and 8, the invention 10 is shown in its in use position in conjunction with a tooth T to be repaired. Whenever the repair cavity T' is sufficiently extreme as to require the dentist or dental practitioner to extend the tooth material removal site out to and through a side of the tooth, a cavity T" is also produced. These two combined cavities T' and T" must then be filled with a suitable amalgam or permanent repair filler material to refill those cavities.

The accepted procedure for effecting the installation of this repair material is to temporarily install a matrix band MB around the tooth T and down to the gum area, after which the matrix band MB is tightened in place by associated well-known clamping mechanisms attached thereto. It is at this point that the invention 10 comes into play. Without the aid of the present invention 10, the lower matrix band margin MB' as depicted in FIG. 6 and 8 typically will catch on the gingival margin G' of cavity T", preventing further progressive installation movement of the matrix band MB around the tooth T until this obstruction is surmounted.

To facilitate both releasing the lower matrix band margin MB' from the gingival shoulder G, and also to facilitate further progressive installation of the matrix band MB around the tooth T in preparation for repair, the guide blade 20 is positioned as shown between the tooth T and the matrix band MB and wherein the bracket 28 engages the upper margin of the matrix band MB as shown.

The importance of the interrelationship between the distal end or tip 24 and the lower matrix band margin MB' may be now appreciated when one understands that the tip 24 will conveniently extend below the gingival shoulder G and also below the lower matrix band margin MB'. By this arrangement, then, the distal tip portion 24, pressing against the side of the tooth T below the gingival shoulder G conveniently "shoehorns" the lower matrix band margin MB' around and outwardly of the gingival margin G, whereupon downward pressure via the handle 12 conveniently allows the guide blade 20 to then progressively move the matrix band MB into its final position wherein the lower matrix band margin MB' is against the gums.

In some situations, it may be helpful to flex the relatively thin surgical stainless steel matrix band MB outwardly to further enhance and facilitate the progressive installation thereof. Therefore, bend 26 is provided to effect this outward bending or flexing of the matrix band MB as best seen in FIGS. 6 and 8.

As best seen in FIG. 7, the overall contour of the relatively thin, yet rigid guide blade 20 is curved with the convex surface having the bracket 28 attached as previously described. By this configuration of transverse cross section then, the guide blade 20 may be conveniently placed against the relatively curved sides of the tooth T to enhance stabilization and quick positioning of the guide blade 20 to further enhance the effectiveness of this invention.

It should be again noted that the orientation of the guide blade 20 and the particular degree of bends at 22 and 26, as well as the orientation of first offset 18, may be varied so as to provide a dental instrument each of which will conveniently function for the mesial (front), distal (rear), buccal (outer), and lingual (inner) surfaces of any given tooth to be repaired. Each dental instrument may, then, have a different configuration of these components to provide a dual-ended instrument for effecting any combination of two of the side repairs desired.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A dental instrument for assisting in the temporary placement of a dental matrix band around a tooth to be repaired comprising:
    an elongated slender handle having a first and second end and adapted to be grasped and manipulated by a user's hand;
    a thin matrix band guide blade disposed from said handle first end;
    said guide blade having an upper portion adjacent said handle first end and a wider mid-portion tapering to a generally pointed distal end;
    said guide blade having a generally curved transverse cross section whose generally concave surface is adapted to mate against a side of the tooth;
    said guide blade also having a first transverse bend across said mid-portion and a bracket extending outwardly from the convex surface of said mid-portion, said bracket adapted to engage the upper margin of the matrix band and retain the matrix band against said guide blade generally convex surface during positioning of the matrix band around the tooth to be repaired and its associated gingival margin shoulder;
    said first bend disposing said mid-portion therebelow in the direction of said concave surface;
    said guide blade also having a second transverse bend below said first bend and said bracket and adjacent said distal end, said second bend in the same direction as said first bend;
    the distance between said guide blade distal end and said bracket slightly greater than the width of the matrix band.

2. A dental instrument as set forth in claim 1, wherein:
    said guide blade is positioned in relation to said handle such that said guide blade may be manipulated between the matrix band and the tooth mesial surface.

3. A dental instrument as set forth in claim 1, wherein:
    said guide blade is positioned in relation to said handle such that said guide blade may be manipulated between the matrix band and the tooth distal surface.

4. A dental instrument as set forth in claim 1, wherein:
    said guide blade is positioned in relation to said handle such that said guide blade may be manipulated between the matrix band and the tooth buccal surface.

5. A dental instrument as set forth in claim 1, wherein:
said blade guide also has a generally concave-shaped transverse cross section adapted to mateably fit against a side of the tooth lingual surface.

6. A dental instrument as set forth in claim 1, further comprising:
a second guide blade disposed from said handle second end;
said second guide blade oriented inrelation to said handle differently from said guide blade to accommodate gingival margin shoulder repair on a different side of the tooth.

7. A dental instrument as set forth in claim 6, wherein:
said guide blade and said second guide blade are adapted for use in conjunction with repair to the buccal and lingual tooth surfaces.

8. A dental instrument as set forth in claim 6, wherein:
said guide blade and said second guide blade are adapted for use in conjunction with repair to the distal and mesial tooth surfaces.

* * * * *